US00PP07771P

United States Patent [19]

Saville

[11] Patent Number: Plant 7,771

[45] Date of Patent: Jan. 21, 1992

[54] MINIATURE ROSE PLANT NAMED SAVANICE

[75] Inventor: F. Harmon Saville, Rowley, Mass.

[73] Assignee: Nor'East Miniature Roses, Inc., Rowley, Mass.

[21] Appl. No.: 591,131

[22] Filed: Oct. 1, 1990

[51] Int. Cl.[5] ..... A01H 5/00

[52] U.S. Cl. ..... Plt./9

[58] Field of Search ..... Plt./9

*Primary Examiner*—James R. Feyrer

*Attorney, Agent, or Firm*—Christie, Parker & Hale

[57] ABSTRACT

A new miniature rose with white flowers of good form.

1 Drawing Sheet

SUMMARY OF THE INVENTION

The present invention relates to a new and distinct variety of rose plant of the miniature rose class, which was discovered by me as a sport in a controlled planting of the variety known as "Cupcake" (U.S. Plant Pat. No. 4,835). The varietal denomination of this new rose is "Savanice".

Among the novel characteristics possessed by this new variety which primarily distinguishes it from its parent and all other varieties of which I am aware is its clean white flowers. In other respects the new variety resembles its parent. The parent variety "Cupcake" produces clear pink flowers and has been accepted in the market place as an exhibition-type miniature rose of the pink color class. There is a need for a similar-appearing variety in the white color class and the new variety satisfies this need.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF THE PREFERRED EMBODIMENT

The following is a detailed description of my new variety, with color terminology in accordance with the Royal Horticultural Society Colour Chart (R.H.S.C.C.). The terminology used in color description herein refers to plate numbers in the aforementioned color chart, e.g., "15B" is plate "15B" of the Royal Horticultural Society Colour Chart.

Parentage: Sport (mutation) of the miniature rose known as "Cupcake."

Class: Miniature.

The following observations are made of specimens grown under glass in Essex County, Mass., during the month of July.

FLOWER

Blooming habit: Continuous.

A. Bud:
- (1) *Size.*—Medium.
- (2) *Form.*—Ovate.
- (3) *Color.*—As sepals divide, bud color is from near 155D.
- (4) *Sepals.*—Smooth, short, slight foliation.
- (5) *Peduncle.*—Length — about ¾ to 1½ inches. Aspect — straight. Strength — strong. Color — near 145A.

B. Bloom:
- (1) *Size.*—Average size when fully expanded — about 1¼ to 1½ inches.
- (2) *Borne.*—Singly, one to a stem and in sprays of 5 to 8 blooms.
- (3) *Form.*—High centered at first; outer petals roll under; some petals quill to points.
- (4) *Petalage.*—Number of petals under normal conditions — about 55 to 60.
- (5) *Color.*—After sepals fall and petals unfurl, predominant flower color is near 155D. Flowers retain clean white coloring as petals open. Slight, very light pink cast, near 36D, may be seen where petals bunch. Consistent white coloring remains after three or more days. General tonality from a distance is white. Color at point of petal attachment is near 155A.

C. Petals:
- (1) *Texture.*—Firm.
- (2) *Appearance.*—Inside satiny and outside satiny.
- (3) *Form.*—Rounded; petals relatively wide in older blooms; some pointed apices.
- (4) *Arrangement.*—Regularly arranged, imbricated.
- (5) *Petaloids in center.*—10–15.
- (6) *Persistence.*—Drop off cleanly.
- (7) *Fragrance.*—Slight.
- (8) *Lasting quality.*—Lasting quality on plant is very long, slightly less as cut flower.

REPRODUCTIVE ORGANS

A. Stamens, filaments and anthers:
- *Arrangement.*—Regularly arranged around styles.
- *Color.*—Orange yellow filaments.

B. Pollen:
- *Color.*—Orange yellow.

C. Styles: Uneven, medium length.

D. Stigmas:
- *Color.*—Greenish yellow.

E. Hips: None observed.

PLANT

A. Form: Compact, rounded.

B. Growth: Very vigorous, uniform branching.
*Height attained.*—About 12 to 15 inches.

C. Foliage: Compound 5 to 7 leaflets.
(1) *Size.*—Medium.
(2) *Quantity.*—Abundant.
(3) *Color.*—New foliage: Upper side — near 131A. Under side — near 131A. Old foliage: Upper side — near 131A. Under side — near 131A.
(4) *Shape.*—Oval, pointed.
(5) *Texture.*—Upper side is glossy; under side is matte.
(6) *Edge.*—Serrate.
(7) *Serration.*—Large.
(8) *Leaf stem.*—Color — near 152A. Under side — 144C.
(9) *Stipules.*—Medium length.
(10) *Resistance to disease.*—Blackspot — Average. Mildew — Average. Rust — Average.

D. Wood:
(1) *New wood.*—Color — near 143C. Bark — smooth.
(2) *Old wood.*—Color — near 144A. Bark — smooth.

E. Thorns:
*Quantity (main stalk).*—Almost none.
*On laterals from stalk.*—Practically none.
*Form.*—Short, thin, pointed.
*Length.*—Short.
*Color.*—Near 161B.
*Position.*—Irregular and rare.
*Prickles.*—None.

F. Winter hardiness: Needs protection in severe climates.

I claim:

1. A new and distinct variety of rose plant of the miniature rose class, substantially as shown and described, characterized particularly by attractive white flowers of good form.

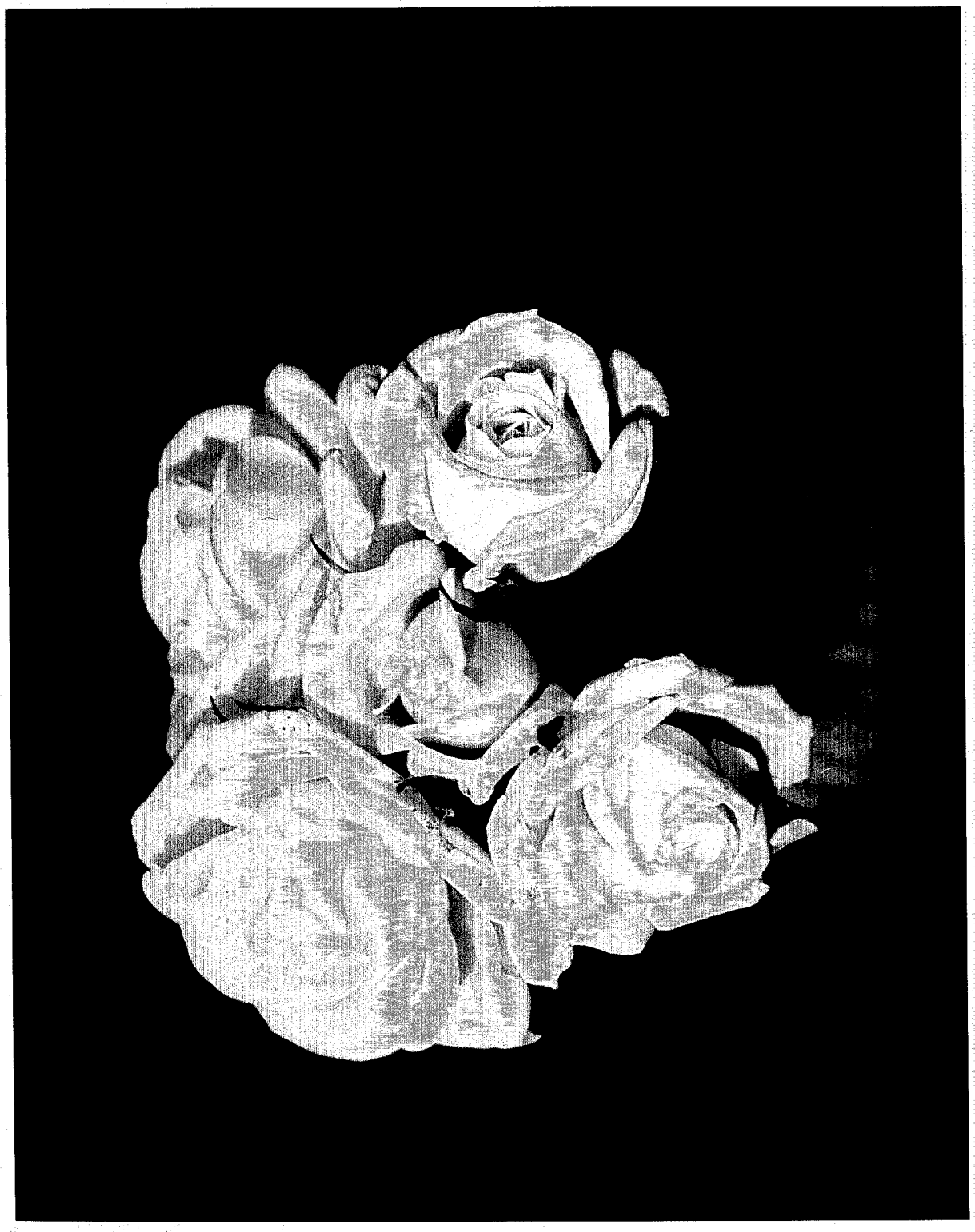

* * * * *